(12) United States Patent
De Wael et al.

(10) Patent No.: US 9,594,047 B2
(45) Date of Patent: Mar. 14, 2017

(54) POTENTIOMETRIC SENSORS AND METHOD FOR MEASURING INTERMOLECULAR INTERACTIONS

(71) Applicant: Universiteit Antwerpen, Antwerp (BE)

(72) Inventors: Karolien De Wael, Sint-Gillis-Waas (BE); Lucien Nagels, Heffen (BE); Guido Van Camp, Duffel (BE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 309 days.

(21) Appl. No.: 14/254,542

(22) Filed: Apr. 16, 2014

(65) Prior Publication Data

US 2014/0318985 A1    Oct. 30, 2014

Related U.S. Application Data

(60) Provisional application No. 61/816,401, filed on Apr. 26, 2013.

(51) Int. Cl.
*G01N 27/327*    (2006.01)
*G01N 27/333*    (2006.01)
(Continued)

(52) U.S. Cl.
CPC ....... *G01N 27/3335* (2013.01); *G01N 27/327* (2013.01); *G01N 27/40* (2013.01); *G01N 33/54353* (2013.01)

(58) Field of Classification Search
CPC .. G01N 27/333; G01N 27/3335; G01N 27/40; G01N 27/327; G01N 27/3275; G01N 27/3276; G01N 27/48
See application file for complete search history.

(56) References Cited

U.S. PATENT DOCUMENTS

| 4,653,499 A | * | 3/1987 | Murray, Jr. ........ | G01N 27/3335 600/348 |
| 4,973,294 A | * | 11/1990 | Kobari .................... | B62D 9/00 475/150 |
| 6,770,190 B1 | * | 8/2004 | Milanovski ........ | G01N 33/5438 205/777.5 |

FOREIGN PATENT DOCUMENTS

| WO | WO 96/02001 A1 | * | 1/1996 | .......... G01N 33/543 |
| WO | WO 97/15827 A1 | * | 5/1997 | .......... G01N 27/327 |

OTHER PUBLICATIONS

Pilehvar, Sanaz, et al., "Aptasensing of Chloramphenicol in the Presence of Its Analogues: Reaching the Maximum Residue Limit," Analytical Chemistry, 2012, vol. 84, pp. 6753-6758.
(Continued)

*Primary Examiner* — Alexander Noguerola
(74) *Attorney, Agent, or Firm* — Duane Morris LLP; J. Rodman Steele, Jr.; Gregory M. Lefkowitz

(57) ABSTRACT

A coated-wire potentiometric sensor comprising an electronically conducting substrate electrode coated with an ionically conductive sensing layer and an outermost surface consisting of or comprising in and/or on a first molecular species which is capable of reversibly adsorbing a second molecular species and a method for measuring the affinity between a first molecular species and a second molecular species comprising the steps of: providing a potentiometric sensor of the coated-wire type having an outermost surface; adapting said outermost surface so that consists of or comprises said first molecular species; placing said sensor in a system for the recording of sensorgrams; recording a sensorgram of the adsorption of a second molecular species on said first molecular species of or comprised in and/or on said adapted outermost surface.

25 Claims, 8 Drawing Sheets

(51) Int. Cl.
  *G01N 27/40*  (2006.01)
  *G01N 33/543* (2006.01)

(56) References Cited

OTHER PUBLICATIONS

De Wael, Karolien, et al., "The Electrochemistry of a Gelatin Modified Gold Electrode," Int. J. Electrochem. Sci., 2011, vol. 6, pp. 1810-1819.
Sassolas, Audrey, et al., "Electrochemical Aptasensors," Electroanalysis, 2009, vol. 21, No. 11, pp. 1237-1250.
Lu, Ying, et al., "Aptamer-based electrochemical sensors that are not based on the target binding-induced conformational change of aptamers," Analyst, 2008, vol. 133, pp. 1256-1260.
Swensen, James S., et al., "Continuous, Real-Time Monitoring of Cocaine in Undiluted Blood Serum via a Mircofluidic, Electrochemical Aptamer-Based Sensor," J. Am. Chem. Soc., 2009, vol. 131, pp. 4262-4266.

* cited by examiner

POTENTIOMETRIC SENSORS AND METHOD FOR MEASURING INTERMOLECULAR INTERACTIONS

CROSS-REFERENCE TO RELATED APPLICATION

This application claims priority to U.S. Provisional Application No. 61/816,401, filed Apr. 26, 2013, the entire content of which is incorporated herein by reference.

TECHNICAL FIELD OF THE INVENTION

The present invention relates to coated-wire potentiometric sensors, a method for measuring therewith the affinity between a first molecular species thereon and a second molecular species and a process using a coated-wire potentiometric sensor to measure the surface concentration of a second molecular species adsorbed on a first molecular species thereon.

BACKGROUND OF THE INVENTION

The present gold standard for measuring the affinity between two (bio)molecules (called ligands) is surface plasmon resonance (SPR) [see Schasfoort, R. B. M., Tudos, A. J., Handbook of Surface Plasmon Resonance; Royal Society of Chemistry: Cambridge, U.K. (2008)]. One of the ligands is bound to a surface layer (the "bait" layer) which is mounted in a microfluidics device. The other ligand (the "prey") is injected as a square concentration pulse at different concentrations. Association/dissociation rates, and binding constants, can be calculated from the output signal after application of an adsorption binding kinetics model. The quartz microbalance (QMB, see Liu, Y., Jaiswal, A., Poggi, M. A., Wilson, W. D., Surface Plasmon Resonance and Quartz Crystal Microbalance Methods for Detection of Molecular Interactions; and in Chemosensors: Principles, Strategies, and Applications; Wang, B., Anslyn, E. V., Eds.; John Wiley & Sons Inc.: Hoboken, N.J., 2011; Chapter 16), evanescent wave sensors (see Strehlitz, B.; Nikolaus, N.; Stoltenburg, R., Sensors 2008, 8, 4296-4307) and affinity chromatographic systems [see Tong, Z. H.; Schiel, J. E.; Papastavros, E.; Ohnmacht, C. M.; Smith, Q. R.; Hage, D. S., J. Chromatogr. A 1218, 2011, 2065-2071] are also able to yield quantitative information on the affinity between ligands (see Nienhaus, G. U. Protein-Ligand Interactions: Methods And Applications; Humana Press: Totowa, N.J., 2005). These techniques, which are still in full scientific development, do not require fluorescent labeling (label-free) or extensive sample cleanup. They can be used in fluidic environments.

Potentiometric techniques rely on the development of a potential over a membrane. These potentials are often created by adsorption/diffusion phenomena taking place at the sensor surface. A recent expert update of ideas in the discussion of how these potentials are created is given by Lewenstam [see Lewenstam, A. J., Solid State Electrochem. 15 (2011) 15-22]. Changes of potentials at all kinds of surfaces are well-known in nature's colloidal systems and biomembrane structures. In analytical laboratories potentiometry is mostly performed with ion-selective electrodes (ISEs). The market for such sensors is very extensive, and especially for biomedical and microbiological research, they are part of highly automated equipment with high sample throughput. Several groups have shown that it is possible to use them for targeting charged organic molecules [see Bakker, E.; Pretsch, E. Angew. Chem., Int. Ed. 46 (2007) 5660-5668; and Stefan-van Staden, R. I.; van Staden, J. F.; Aboul-Enein, H. Y. Anal. Bioanal. Chem. 394 (2009) 821-826], multiply charged polymeric and oligomeric substances [see Fu, B.; Bakker, E.; Yun, J. H.; Wang, E.; Yang, V. C.; Meyerhoff, M. E., Electroanalysis 7 (1995) 823-829; and Nagels, L. J.; Everaert, J.; Bohets, H.; Del Favero, J.; Goossens, D.; Robbens, J.; Pietraszkiewicz, M.; Pietraszkiewicz, O. Comb. Chem. High Throughput Screening 10 (2007) 555-559], and even bioparticles [see Tang, D. P.; Yuan, R.; Chai, Y.; Fu, Y.; Dai, J.; Liu, Y.; Zhong, X., Biosens. Bioelectron. 21 (2005) 539-548].

There is a need for an alternative more accessible technique for studying the molecular interactions of (bio)molecules.

SUMMARY OF THE INVENTION

It is an object of the present invention to provide an alternative technique for studying the molecular interactions of (bio)molecules.

It has been found that potentiometric sensors of the coated-wire type respond to the analytes according to pure adsorption kinetics controlled phenomena, exhibiting adsorption/desorption kinetics which can be studied using sensorgram methodology and provide an alternative to and complement surface plasmon resonance methods in the study of molecular interactions in liquid environments using sensorgram methodology. This research indicates congruence and complementarity between potentiometric (electrochemical) and SPR (optical) methods. This finding opens up totally new application areas for potentiometric sensors in the strongly emerging field of the study of (bio)molecular interactions.

The sensors are placed in a hydrodynamic wall jet system for recording the sensorgrams and the millivolt sensor responses are first converted to a signal, expressing the concentration of adsorbed organic ions enabling binding kinetics to be determined. Using a linearization method, a pseudo-first order-kinetic model of adsorption was shown to fit the experimental results perfectly and $K_{assoc}$, $k_{on}$, and $k_{off}$ values could be calculated. The technique can be used over four decades of concentration and is very sensitive both to low-molecular weight compounds and to multiply-charged large biomolecules as is shown in the invention examples with a lipophilic rubber-based and a collagen-based hydrogel sensor coating for the molecules promazine, lidocaine, tartaric acid and dopamine respectively.

The objects of the present invention are provided by the first, second and third aspects of the present invention.

A first aspect of the present invention provides a coated-wire potentiometric sensor comprising an electronically conducting substrate electrode coated with an ionically conductive sensing layer and an outermost surface consisting of or comprising in and/or on a first molecular species which is capable of reversibly adsorbing a second molecular species.

A second aspect of the present invention provides a method for measuring the affinity between a first molecular species and a second molecular species comprising the steps of: providing a potentiometric sensor of the coated-wire type having an outermost surface; adapting said outermost surface so that consists of or comprises said first molecular species; placing said sensor in a system for the recording of sensorgrams; recording a sensorgram of the adsorption of a second molecular species on said first molecular species of or comprised in and/or on said adapted outermost surface.

A third aspect of the present invention provides a process using a coated-wire potentiometric sensor comprising an electronically conducting substrate electrode coated with an ionically conductive sensing layer and an outermost surface, which has been adapted to consist of or comprise in and/or on a first molecular species to measure the surface concentration of a second molecular species by converting the millivolt sensor responses to the concentration of said adsorbed second molecular species.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
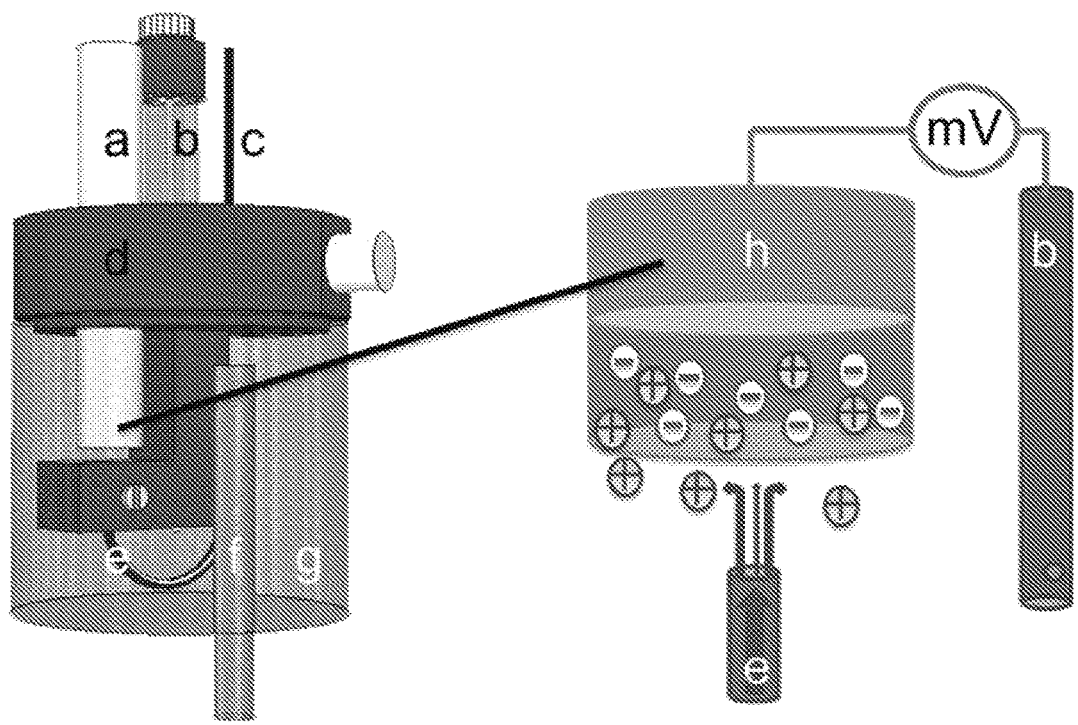
FIG. 1 is a schematic representation of a potentiometric "coated wire" sensor setup components in a "large-volume" wall-jet cell in which buffer eluent is continuously sprayed through HPLC tubing [(c) indicates the injector side and (e) the sensor side] onto the sensor (a) coating and hits an ionically conducting sensing layer (rubber type or gelatin in the present invention) which is connected to an electronically conducting substrate material (h), which itself is electrically connected to a reference electrode (b) via a high-impedance voltmeter. The outlet tubing (f) is part of the glass cell (g). All components are mounted in a PVC head (d).

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms are provided solely to aid in the understanding of the invention.

DEFINITIONS

The term "molecular species", as used in disclosing the present invention, includes non-macromolecular and macromolecular molecules. In the context of the present invention molecules are referred to as ligands.

The term "first molecular species" is to distinguish the molecules of the first molecular species from those of the second molecular species. The first molecular species can be a non-macromolecular or molecular species involved in the adaption of the outermost surface of the potentiometric sensor or a species immobilised therein and/or adsorbed thereon with the provision that it is accessible for adsorption of the second molecular species so that there is molecular interaction between the first and second molecular species. The molecules of the first molecular species are different from those of the second molecular species.

The term "biomolecule" as used in disclosing the present invention, is an organic molecule occurring in living organisms, especially a macromolecule, e.g. amino acids, lipids, nucleic acids, proteins, polysaccharides, DNA, and RNA.

The term "biomolecular", as used in disclosing the present invention, means pertaining to organic molecules occurring in living organisms, especially macromolecules.

The term "bio-active agent or biologically-active molecule", as used in the present application, includes any compound, composition of matter, or mixture thereof, that has biological activity, whether occurring naturally or synthesised.

The term "sensorgram", as used in disclosing the present invention, means a plot of the potentiometric signal vs. time, when a square concentration (block) pulse passes the sensor.

The term "sensorgram methodology", as used in disclosing the present invention, means the use of the sensorgram to calculate $K_{assoc}$ values (the equilibrium coefficient of association of one molecular species to another) for the interaction between molecules, using an adsorption/desorption model.

The term electrochemical aptasensor, as used in disclosing the present invention, means an Electrochemical sensor with immobilized aptamers as sensing elements e.g. as target molecules for bio(recognition) elements.

The term aptamer [single strand (ss)DNA or RNA], as used in disclosing the present invention, means a synthetic oligonucleic acid sequence which can bind to its target with high affinity and specificity due to its flexibility.

The term DNA-aptamer, as used in disclosing the present invention, means a single string (ss) artificial nucleic acid i.e. synthetic oligonucleic acid sequence which has been designed specifically to recognise and bind a particular molecular target such as a small molecule, a protein, a nucleic acid, a cell, tissue or an organism with high affinity and specificity due to their flexibility that results in binding to their ligands via adaptive recognition involving conformational alteration.

The term hydrophilic, as used in disclosing the present invention, means having an affinity for attracting, adsorbing or absorbing water.

The term hydrogel, as used in disclosing the present invention, is a colloid in which the disperse phase (colloid) has combined with the continuous phase (water) to produce a viscous jellylike product e.g. coagulated silicic acid and a two- or multicomponent systems consisting of a three-dimensional network of polymer chains and water that fills the space between macromolecules. Depending on the properties of the polymer (polymers) used, as well as on the nature and density of the network joints, such structures in an equilibrium can contain various amounts of water; typically in the swollen state the mass fraction of water in a hydrogel is much higher than the mass fraction of polymer. Two general classes of polymeric hydrogels can be defined—physical gels (pseudogels), where the chains are connected by electrostatic forces, hydrogen bonds, hydrophobic interactions or chain entanglements (such gels are non-permanent and usually they can be converted to polymer solutions by heating) and chemical (true, permanent) hydrogels with covalent bonds linking the chains. In this paper we deal with the formation and applications of permanent polymer networks. Hydrogels must be able to hold, in equilibrium, certain amounts of water. This implies that the polymers used in these materials must have at least moderate hydrophilic character. In practice, to achieve high degrees of swelling, it is common to use synthetic polymers that are water-soluble when in non-crosslinked form. Typical simple materials applied for general-purpose hydrogels are poly(ethylene oxide), poly(vinyl alcohol), polyvinylpyrrolidone and poly(hydroxyethyl methacrylate). Although majority of hydrogels for biomedical purposes are made of synthetic polymers, there are also numbers of examples where crosslinked natural polymers, mainly polysaccharides, are applied.

The abbreviation DA, as used in disclosing the present invention, represents dosamine. DA is a cationic drug of the catecholamine family which was discovered in 1950. This neurotransmitter has a variety of functions in the nervous system and is also important in the problematics of drug addiction, Parkinson- and Alzheimer's disease (B. E. Rekha, Int. J. Electrochem. Sci. 4 (2009) 832-845.

The abbreviation SELEX, as used in disclosing the present invention, represents "selection evolution of ligands by exponential enrichment".

The abbreviation EIS, as used in disclosing the present invention, represents Electrochemical impedance spectroscopy.

The abbreviation SPR, as used in disclosing the present invention, represents Surface Plasmon Resonance.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Potentiometric Coated Wire Sensors

A first aspect of the present invention provides A coated-wire potentiometric sensor comprising an electronically conducting substrate electrode coated with an ionically conductive sensing layer and an outermost surface consisting of or comprising in and/or on a first molecular species which is capable of reversibly adsorbing a second molecular species.

According to a preferred embodiment of the first aspect of the present invention, said outermost surface is adapted with a coating immobilising said first molecular species.

According to another preferred embodiment of the first aspect of the present invention, said outermost surface is adapted with a hydrogel coating immobilising said first molecular species, the hydrogel coating being preferably a collagen-based hydrogel and particularly preferably gelatin.

According to another preferred embodiment of the first aspect of the present invention, at least one of said first and second molecular species is selected from the group consisting of target molecules for bio(recognition) elements, macrocycles, ionophores, proteins, antibodies, bioparticles (viruses, bacteria, . . . ), DNA, and aptamers.

According to another preferred embodiment of the first aspect of the present invention, said outermost surface is adapted with a hydrogel coating on which said first molecular species is adsorbed, said hydrogel coating being preferably a collagen-based hydrogel and particularly preferably gelatin.

According to another preferred embodiment of the first aspect of the present invention, said outermost surface is adapted with a lipophilic rubber-based coating.

According to another preferred embodiment of the first aspect of the present invention, said outermost surface is adapted with a collagen-based hydrogel coating.

Various coupling procedures are known to bind aptamers to coatings. For example in the case of gelatin ethyl-dimethyl-aminopropylcarbodiimide (EDC) and N-hydroxy succinimide (NHS) can be used as coupling agents.

The sensing layer and the substrate electrode should provide for good ion-to-electron conversion. Several interesting combinations of materials and methods to measure their effectiveness are described in the literature to obtain these characteristics: see the section "Potentiometric Electrode".

As part of the indicator electrode a PVC cylinder containing a cylindrical electrode, which is an electronically conducting graphite/PVC composite material is exemplified, see FIG. 1 part "h". However, other conductive materials known to the person skilled in the art can be used for the electrode e.g. gold electrodes (with linking agents), glassy carbon, glassy carbon coated with a conductive polymer such as polypyrrole, polyaniline polyacetylene and poly(3, 4-ethylenedioxythiophene) (PEDOT).

The substrate material in FIG. 1 (part "h") contains graphite particles (see Nagels, L. J.; Bohets, H.; Jimidar, M. Potentiometric electrode, gradient polymer, uses and method of preparation therefor. U.S. Pat. No. 7,857,962 B2) which are effective ion-to-electron transducers when used in certain conditions [see Mattinen, U.; Rabiej, S.; Lewenstam, A.; Bobacka, J. Electrochim. Acta 56 (2011) 10683-10687]. The sensing layer can be an ionically conductive coating which contacts the analyte solution at one side, and the substrate material (h) at the other side: see FIG. 1, right side. In the example of FIG. 1, the ionically conducting layer contains a large lipophilic anion. The countercation (usually small and hydrophilic) is the cation which is present in (and exchanged with) the contacting running buffer solution.

The potential is monitored by a high-impedance voltmeter, placed between the electronically conducting substrate electrode and a reference electrode (b in FIG. 1) which also contacts the analyte solution. In our situation, the sensor is part of a large-volume wall jet flow cell in an FIA setup: see the section "Flow Injection Analysis Sensorgrams" and FIG. 1. The liquid flow is directed perpendicularly to the ionically conducting coating layer.

The ionically conducting layer is an ion-exchange material. In the case of FIG. 1, the large lipophilic anion has a more or less permanent position in the layer. The small hydrophilic cation, on the other hand, is free to move also into the analyte (second molecular species) solution. Such materials are accessible to cationic but not anionic substances: they are permselective. They are known to develop a surface charge as the mobile cations tend to diffuse in the contacting solution (see Lewenstam, A., Solid State Electrochem. 15 (2011) 15-22). This tendency provokes a charge separation, which results in a potential difference mainly at the coating/analyte (second molecular species) solution interface. Further diffusion stops when the developed electrical energy balances the tendency of the ions to distribute themselves over the interface. A Bolzmann (Gibbs) type of statistical mechanics reasoning will lead to the Nernst equation to calculate the developed potential (see Hobbie, R. K. Intermediate Physics for Medicine and Biology; Springer-Verlag: New York, 1997). When properly chosen positively charged analyte ions are added to the running buffer, they can change the interface potential between the ionically conductive coating and the sample solution. Adsorption as well as ion exchange of the analyte ion can be expected to take place at the sensing layer. These phenomena will alter the interface potential. In the short time conditions of sensorgram recordings, adsorption may be dominant. Again, the laws of statistical mechanics will lead to a Boltzmann factor and its equivalent, the Nernst equation, to describe the developed potential versus the analyte concentration. The Nernst equation states that the potential difference which is obtained at the solution/sensing layer interface implies a certain ratio for the analyte in the solution over its concentration in the sensing layer:

$$\Delta E(V) = \frac{RT}{zF} \ln \frac{c_{a,solution}}{c_{a,sensing\ layer}} \quad (1)$$

It results in a logarithmic dependence of the developed interface potentials on the concentration of analyte ion with variable concentration at one side of the interface. In our case, this is the analyte concentration in the solution, $c_{a,solution}$. The equation is mostly written for a temperature of 25° C. and in the log(not ln) form:

$$\Delta E(mV) = \frac{59}{zF} \log(c_{a,solution}) = S \log(c_{a,solution}) \quad (2)$$

S being used as the "slope", here 59 mV, divided by zF. zF is the charge per particle present in the potential-forming process. In Bazylak, G.; Nagels, L. J. J. Pharm. Biomed. Anal. 32 (2003) 887-903 it was found that with large multiply charged macromolecules (DNA) that this is not necessarily the total number of charges on the molecule, but a fraction thereof. This has to do with the fact that the Boltzmann factor (and the Nernst equation derived from it) deals with point charges [see Greathouse, J. A.; Feller, S. E.; McQuarrie, D. A., Langmuir 10 (1994) 2125-2130]. Another point of attention is the fact that activities should be used in equation 2, but in our experimental conditions, using molar concentrations in the equations worked perfectly.

The analyte ion (second molecular species) is never the sole species which causes potential differences to develop over the interface. Interferences from other ions become important at low analyte concentrations. In the present study, the buffer ions in solution are the interfering ions. The influence of interfering ions on the developed potential was expressed in a much used equation, which was derived semi-empirically by Nicolskii-Eisenmann. A variant of this equation is applicable under our experimental conditions:

$$\Delta E(mV) = E^0 + S \log(c_{a,solution} + Cst) \quad (3)$$

Figure 4:
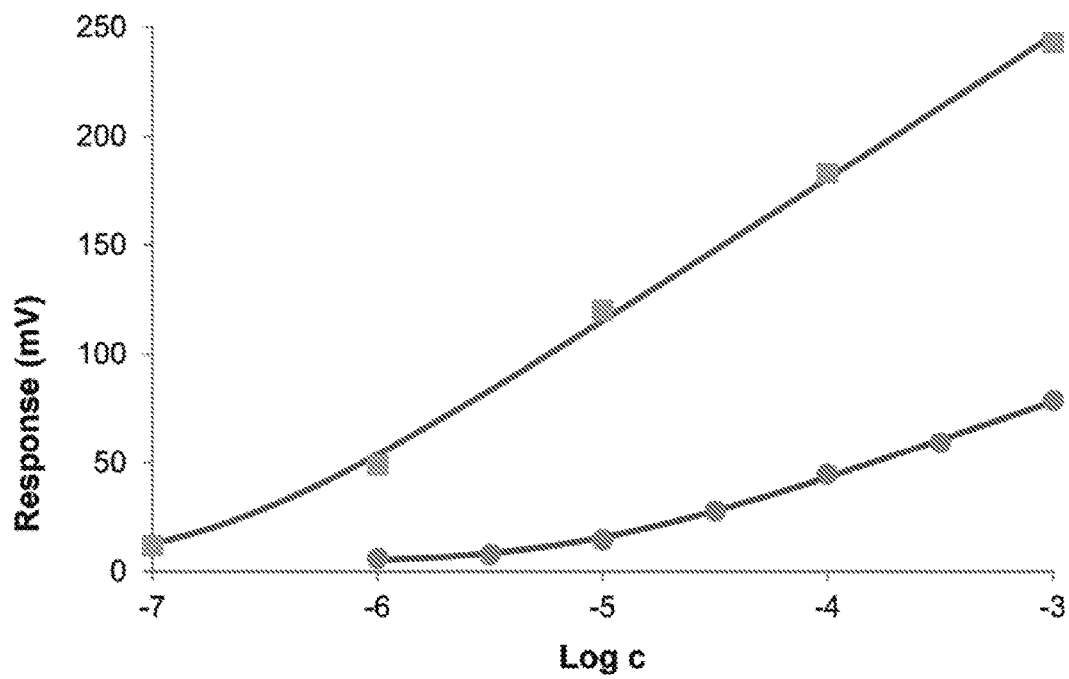
FIG. 4 shows Nicolskii-Eisenmann-type calibration graphs: lower curve, data for the tartaric acid/gelatin sensor combination; upper curve, data for the promazine/PVC sensor combination. Measured data are labeled with circles and squares respectively. The smooth curves are nonlinear least-squares fits to Nicolskii-Eisenmann functions. The standard deviations on the experimentally determined values are ≤2% (three measurements per concentration).

The potential output is logarithmically dependent on $c_{a,solution}$ at higher analyte (second molecular species) concentrations. At low analyte concentrations, the buffer ions become the potential-determining ions. As their concentration is constant in our case, their contribution to the potential output (mV) is constant. We therefore just add the term "Cst" in equation 3. The validity of equation 3 was verified in our laboratory with numerous organic ionic compounds using nonlinear least-squares fittings, and it always closely described the situation for concentrations lower than $10^{-3}$ M (see also FIG. 4 in the Discussion). The Nicolskii-Eisenmann equation (eq 3) has a complex relationship between the millivolt output of potentiometric sensors and $c_{analyte}$ if the low analyte concentrations have to be included (see Bakker, E.; Pretsch, E. Angew. Chem., Int. Ed. 46 (2007) 5660-5668).

Sekula, J.; Everaert, J.; Bohets, H.; Vissers, B.; Pietraszkiewicz, M.; Pietraszkiewicz, O.; Du Prez, P.; Vanhoutte, K.; Pruss, P.; Nagels, L. in Anal. Chem., 78 (11) (2006) 3772-3779 disclosed the transpose of the NE equation:

$$c_{analyte} = (10^{mV/S} - 1) Cst \quad (4)$$

To keep this equation simple, the output of the sensor is offset to 0 mV at $c_{analyte} = 0$, a condition which can be handled easily in practice. The term $10^{mV/S} - 1$ is linearly related to $c_{analyte}$. Equation 4 was studied in detail in our group for several organic cationic and anionic substances and it was found to be valid over concentration ranges varying from $10^{-3}$ to $10^{-7}$ M and below. $10^{mV/S} - 1$ versus $c_{analyte}$ plots recorded in FIA and High performance liquid chromatography (HPLC) applications yielded straight lines with $R^2$ values close to 1. Studying adsorption phenomena (e.g., via sensorgrams in SPR) requires sensor responses which are related to the concentration of adsorbed species. In the conditions used for potentiometric sensors ($10^{-3}$ M analyte solutions and lower), we work in the part of the Langmuir or Freundlich isotherms where $c_{adsorbed}$ is linearly related to the analyte bulk concentration, $c_{analyte}$. This can be deduced from, e.g., experimental measurements of adsorption isotherms for charged organic molecules on mineral ion exchange materials [see Atkin, R.; Craig, V. S. J.; Wanless, E. J.; Biggs, S. J. Colloid, Interface Sci., 266 (2003) 236-244] or on biological tissue materials [see Lovich, M. A.; Edelman, E. R. Biophys. J. 70 (1996) 1553-1559]. Therefore, in our case, the signal or the "response" $R \approx c_{adsorbed} \approx c_{analyte} \approx 10^{mV/S} - 1$ (see equation 4).

In what follows, "response" ("R") will be used to indicate the $10^{mV/S} - 1$ function.

Adsorption Kinetics Model

A model which thoroughly tests adsorption phenomena at different concentrations of analyte is the so-called linearization method (see Schasfoort, R. B. M., Tudos, A. J. Handbook of Surface Plasmon Resonance; Royal Society of Chemistry: Cambridge, U.K., 2008). The method is also sensitive to discovery of the eventual presence of important mass-transfer phenomena, or nonhomogeneous adsorption, which would complicate the derivation of kinetic parameters. De Backer, B. L.; Nagels, L. J. Anal. Chem. 68 (1996)

4441-4445 reported in a study of the large volume potentiometric wall jet detector in analogous hydrodynamic techniques (HPLC), mass transfer rates through the diffusion layer, which were fast enough not to interfere with the presently monitored (much slower) adsorption phenomena. On some occasions, diffusion into the sensing layer (ion exchange) or heterogeneous adsorption sites makes the study more complex. The phenomena are well-known to the SPR users. For the invention examples, no evidence was found for such deviations.

The model is based on the assumption that the rate determining phenomenon is the adsorption of analyte A (second molecular species) to the surface receptor sites $R_{surface}$:

$$A + R_{surface} \rightleftharpoons AR_{surface} \qquad (5)$$

Receptor sites are occupied by the analyte are designated as $R_{occupied}$. The rate of adsorption can be expressed as $v_{on}$:

$$v_{on} = \frac{dR_{occupied}}{dt} \qquad (6)$$
$$= k_{on} c_{analyte}(R_{max} - R_{occupied}) - k_{off} R_{occupied}$$

The process is described by two parts, one for the association phase ("on" kinetics; see equation 6) and one for the dissociation phase ("off" kinetics; see equation 7).

$$v_{off} = -\frac{dR_{occupied}}{dt} = -k_{off} R_{occupied} \qquad (7)$$

"On" kinetics takes place when the sensor is suddenly contacted by a bulk concentration of the analyte, at the onset of the square concentration pulse which moves over the sensor surface. Equation 6 shows that analyte (second molecular species) adsorption rates are determined by the sum of an adsorption component (left term of equation 6) and a desorption component (right term of equation 6). Off kinetics takes place when the analyte concentration suddenly drops to zero (end of the concentration pulse) and pure running buffer solution contacts the sensor. From that moment on, first-order desorption kinetics can occur, described by equation 7.

Differential equation 6 can be solved to yield equations 8 and 10. In these equations, $R_{occupied}$ is replaced by R, the concentration-related response ($10^{mV/S}-1$), as both are linearly related (see above). $R_{max}$ is the value of R which is obtained at the plateau of the sensorgram:

$$R(t) = R_{max}(1 - e^{-k_{obsd}t}) \qquad (8)$$

where $$k_{obsd} = k_{on} c_{analyte} - k_{off} \qquad (9)$$

Equation 7 yields the well-known first-order exponential desorption formula:

$$R(t) = R_{max} e^{-k_{off} t} \qquad (10)$$

These equations are well described in books and in the primary literature (see Schasfoort, R. B. M., Tudos, A. J. Handbook of Surface Plasmon Resonance; Royal Society of Chemistry: Cambridge, U.K., 2008 and Shinohara, Y.; Kim, F.; Shimizu, M.; Goto, M.; Tosu, M.; Hasegawa, Y. Eur. J. Biochem. 223 (1994) 189-194.

It is assumed that the response provoked by the sensor, R, is proportional to the concentration of the complex $AR_{surface}$, i.e., to $R_{occupied}$. In the present case, $R_{occupied} \equiv$ the response of the sensor, R. This is not the mV response output of the sensor but the $10^{mV/S}-1$ response, which is concentration related (see equation 4).

Equation 6 can be transformed into the following equation, which forms the starting point of the linearization method:

$$\frac{dR}{dt} = k_{on} c_{analyte} R_{max} - (k_{on} c_{analyte} + k_{off}) R \qquad (11)$$

Starting from the "association" part of the sensorgram, one can now plot dR/dt versus R. For a pseudo-first-order kinetics, this will yield a straight line with slope equal to $$\text{slope} = -(k_{on} c_{analyte} + k_{off}) \qquad (12)$$

Plotting this slope versus $c_{analyte}$ then yields a graph from which $k_{on}$ and $k_{off}$ can be calculated.

From $k_{on}$ and $k_{off}$, $K_{assoc} = k_{on}/k_{off}$ is obtained, from which $K_{diss}$ ($=1/K_{assoc}$) and the Gibbs free energy of interaction can be calculated ($\Delta G^0 = -RT \ln K_{ass}$). $K_{diss}$ is most frequently used term to express intermolecular interactions. This type of analysis was done for different electrode/analyte combinations. Examples were chosen so as to include examples where the immobilized component (in the coating layer of the sensor) includes large biomolecules (DNA).

Method

A second aspect of the present invention provides a method for measuring the affinity between a first molecular species and a second molecular species comprising the steps of: providing a potentiometric sensor of the coated-wire type having an outermost surface; adapting said outermost surface so that consists of or comprises said first molecular species; placing said sensor in a system for the recording of sensorgrams; recording a sensorgram of the adsorption of a second molecular species on said first molecular species of or comprised in and/or on said adapted outermost surface.

According to a preferred embodiment of the second aspect of the present invention, said outermost surface is provided with a coating immobilising said first molecular species.

According to another preferred embodiment of the second aspect of the present invention, said outermost surface is adapted with a coating on which said first molecular species are adsorbed.

According to a preferred embodiment of the second aspect of the present invention, said outermost surface is adapted with a lipophilic rubber-based coating immobilising said first molecular species.

According to a preferred embodiment of the second aspect of the present invention, said outermost surface is adapted with a hydrogel coating immobilising said first molecular species, the hydrogel coating being preferably a collagen-based hydrogel coating, with gelatin being particularly preferred. According to a preferred embodiment of the second aspect of the present invention, said outermost surface is adapted with a lipophilic rubber-based coating.

According to a preferred embodiment of the second aspect of the present invention, said outermost surface is adapted with a collagen-based hydrogel coating, preferably with gelatin.

According to a preferred embodiment of the second aspect of the present invention, said system is a hydrodynamic wall-jet system.

According to a preferred embodiment of the second aspect of the present invention, at least one of said first and second molecular species is selected from the group consisting of target molecules for bio(recognition) elements, macrocycles, ionophores, proteins, antibodies, bioparticles (viruses, bacteria, . . . ), DNA, and aptamers.

According to a preferred embodiment of the second aspect of the present invention, at least one of said first and second molecular species is a bio-active molecule.

According to a preferred embodiment of the second aspect of the present invention, at least one of said first and second molecular species is a bio-active molecule, which is a pharmacologically active agent.

Process

A third aspect of the present invention provides a process using a coated-wire potentiometric sensor comprising an electronically conducting substrate electrode coated with an ionically conductive sensing layer and an outermost surface, which has been adapted to consist of or comprise in and/or on a first molecular species to measure the surface concentration of a second molecular species by converting the millivolt sensor responses to the concentration of said adsorbed second molecular species.

According to a preferred embodiment of the third aspect of the present invention, wherein said potentiometric sensor is used to measure the adsorption of said second molecular species on said adapted outermost surface as a function of time.

According to another preferred embodiment of the third aspect of the present invention, said concentration of said second molecular species as a function of time is linearized and analysed on the basis of a pseudo-first order-kinetic model of adsorption to provide the $k_{on}$, the rate of association of said second molecular species to said first molecular species, $k_{off}$, the rate of dissociation of said second molecular species from said first molecular species, and $K_{assoc}$, the equilibrium coefficient of association of said second molecular species to said first molecular species.

EXAMPLES

Instrumentation Used

Morphological Investigation:

Investigation of the electrode surface was performed using confocal microscopy by localizing a 58-mer aptamer (see chemicals used section) labeled with a Cy3 dye with a Nikon C1 laser scanning confocal unit (D-eclipse-C1, Nikon, Melville, N.Y.) equipped with an argon and a helium/neon laser line fitted onto an upright microscope (Eclipse E600, Nikon, Melville N.Y.) in combination with a 10× planfluor (NA: 0.50) objective manufactured by Nikon (Melville, N.Y.).

Flow Injection Analysis Sensorgrams:

The flow injection analysis (FIA) recordings were performed using an LC-10ADvp pump (Shimadzu Liquid Chromatography) and a Rheodyne 7125 six-port external sample injector (VICI, Houston, Tex.). A 1.00 mL sample loop was used to generate square concentration pulses for sensorgram recording in FIA conditions. The poly(ether ether ketone) (PEEK) tubing (Alltech, Nicholasville, Ky.) of the injection loop and the injector-detector connections had an internal diameter of 0.18 mm. The flow rate was 1.00 mL min$^{-1}$. Poiseuille peak broadening effects were kept to a minimum using short injector-detector connections (150 mm). To avoid such effects at the end of the square concentration pulse, the injector was switched from inject to load after 40 s (well before the sample loop volume was totally emptied). This results in a sharp pulse with negligible broadening at the start as well as at the end of the pulse.

The eluent was 5.0 mM $H_3PO_4$ (pH 2.4) for the poly(vinyl chloride) (PVC)-based electrodes and 0.5 mM 4-(2-hydroxyethyl)-1-piperazine-ethanesulfonic acid (HEPES; pH 6.0) for the hydrogel electrodes (see the section "Potentiometric Electrode"). The column outlet was directed perpendicularly toward the sensitive membrane of the coated wire electrode in a "wall-jet" flow cell [see FIG. 1 and Bazylak, G.; Nagels, L. J. J. Pharm. Biomed. Anal. 32 (2003) 887-903]. The distance from the LC tubing outlet to the electrode was 0.100 mm unless otherwise stated.

The membrane potential was measured against an Orion 800500 Ross reference electrode (Ag/AgCl) using a high impedance ($10^{13}\Omega$) home-made amplifier. The detection signals were recorded on a data station composed of a PC equipped with a 6013 NI DA converter and LabVIEW 7 (National Instruments, Austin, Tex.) based software. The overall RC time constant of the high-impedance amplifier plus data station was set to 0.200 s.

Potentiometric Electrode:

The indicator electrode was made of a PVC cylinder and contained a cylindrical substrate electrode (3.0 mm diameter×1.0 mm length), which is an electronically conducting graphite/PVC composite material (see Nagels, L. J.; Bohets, H.; Jimidar, M. U.S. Pat. No. 7,857,962 B2). The composite substrate electrode was polished with Carbimet grid 600 (Buehler Ltd., Lake Bluff, Ill.).

The PVC-based working electrodes had a rubber membrane coated on the composite substrate electrode. Electrodes with a composite substrate have the important property that the membrane coating and the composite are tightly mixed at the interface, and sensors constructed in this way show very good impedance characteristics (see Nagels, L; Bohets, H.; Jimidar, M. U.S. Pat. No. 7,857,962 B2). These characteristics were verified using impedance spectroscopy. The measurements were performed with an Autolab Metrohm PGSTAT 128N FRA instrument (frequency 1-100 kHz, amplitude 10 mV). A semicircle in the Nyquist plot was obtained if the electrode had good impedance characteristics. Discussions on such characteristics of potentiometric sensors are well described in Mattinen, U.; Rabiej, S.; Lewenstam, A.; Bobacka, J. Electrochim. Acta 56 (2011) 10683-10687; and Bobacka, J.; Ivaska, A.; Lewenstam, A. Chem. Rev. 108 (2008) 329-351. The coating used for the detection of promazine contained 2% tetrakis(p-chlorophenyl)borate (TCPB), 33% PVC, and 65% dioctyl sebacate (DOS). A 300 mg mass of this mixture was dissolved in 3.00 mL of tetrahydrofuran (THF), and 2×40.0 μL of this solution were applied to the substrate electrode material by drop drying. After evaporation for at least 3 h, the resulting ionically conductive rubber polymer coating had a thickness of 100 μm.

Gelatinous hydrogels were also used as an ionically conducting coating layer. To immobilize the gelatinous hydrogel on the conducting composite electrode substrate, 7.00 μl, of a mixture which consists of 25.0 mg of gelatin A dissolved in 1.00 mL of 0.5 mM HEPES (2.5%, w/v) at 40° C. was brought onto the electrode surface with a micropipet and exposed to air for 2 h at 4° C. [drop drying see De Wael, K.; De Belder, S.; Van Vlierberghe, S.; Van Steenberge, G.;

Dubruel, P. Talanta 82 (2010) 1980-1985]. Sensors constructed in this way show very good impedance characteristics.

The well-known ethyl-dimethyl-aminopropylcarbodiimide and n-hydroxy-succinimide (EDC-NHS) coupling procedure was used (with minor modifications) to bind the aminated aptamer covalently to the hydrogel, which contains carboxyl groups. After adding 20 μL of the coupling agents (15.32 mg of EDC and 2.32 mg of NHS dissolved in 100 μl of 10.0 mM MES buffer at pH 7.0) to the coated hydrogel for 2 h, 2×4 μL of the aptamer ($10^{-4}$M) was applied for 1 h. After evaporation for 2 h, at 4° C. the electrodes were kept in 10.0 mM MES running buffer, pH 7.0.

After the application of the membrane, the electrodes were kept in running buffer (5.0 mM $H_3PO_4$ for the PVC-based electrodes or 0.5 mM HEPES for the hydrogel electrodes) for at least 3 h until a stable baseline was obtained. The sensorgrams of each analyte were measured on three electrodes and used when the inter-electrode reproducibility was better than 10%. At least three sensorgrams (injections) were recorded on each electrode after conditioning and stabilization in the running buffer.

Chemicals Used:

All chemicals were of analytical reagent grade. The FIA eluents were prepared daily by the dilution of a concentrated phosphoric acid solution or by dissolving HEPES, both obtained from Acros Organics (Filter Service NV, Eupen, Belgium). High-molecular-mass PVC was obtained from Janssen Chimica (Beerse, Belgium). The other membrane components were of the highest quality grade available from Fluka (Sigma-Aldrich, Bornem, Belgium). These include plasticizer TCPB, DOS, and the solvent tetrahydrofuran (THF). Type gelatin A (IEP (isoelectric point)=8.8, bloom strength 202), isolated from porcine skin by acid treatment, was obtained from Tessenderlo Chemie (Belgium). Promazine, lidocaine and tartaric acid were obtained from Sigma-Aldrich. A 58 mer aptamer selected specifically to detect DA (Zheng et al., 2011) (5'-GTC-TCT-GTG-TGC-GCC-AGA-GAA-CAC-TGG-GGC-AGA-TAT-GGG-CCA-GCA-CAG-AAT-GAG-GCC-C-spacer-$NH_2$-3') was synthesized by Integrated DNA Technologies (IDT, Leuven, Belgium).

Figure 2:
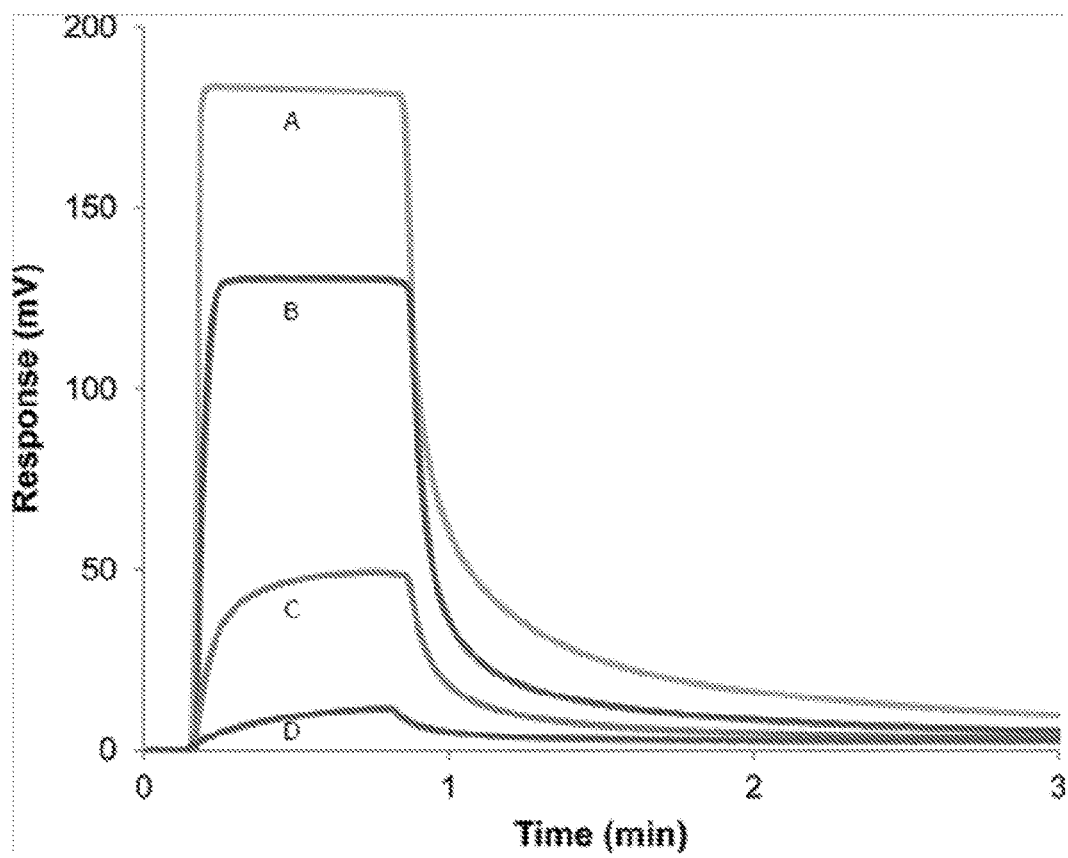
FIG. 2 shows sensorgram recordings for promazine on a PVC-coated sensor. Square concentration profiles were injected for 40 s. The promazine concentrations varied from $10^{-7}$ M (curve D) to $10^{-6}$, $10^{-5}$, and $10^{-4}$ M (curves C, B and A respectively). The y axis is in millivolts, which permits all graphs to be represented in one figure. These graphs were used in the linearization method described in the text.

Linearization Method Applied to a Rubber Phase Coating/Promazine System:

Ionically conductive rubber phase coatings are widely used in robust coated wire potentiometric sensors. When doped with a lipophilic ion such as tetrakis(p-chlorophenyl) borate, the system becomes cation responsive. Lipophilic cationic organic compounds, in particular, will give good signals. Promazine has a log P value of 4.36 (see Vissers, B.; Bohets, H.; Everaert, J.; Cool, P.; Vansant, E. F.; Du Prez, F.; Kauffmann, J. M.; Nagels, L. J. Electrochim. Acta 51, (2006) 5062-5069). Sensorgrams were recorded upon injection in different concentrations as a square concentration pulse in an FIA system, as shown in FIG. 2. The "association" or "on" phase, the plateau region ($R_{max}$), and the "dissociation" or "off" phase are clearly visible.

The sensorgrams have to be plotted with an $R=10^{mV/S}-1$ y axis to have a response (R) which is linearly related to the analyte surface concentration. In FIG. 2, a millivolt y axis is plotted, as this allows the sensorgrams to be represented in one graph. The $10^{mV/S}-1$ versus time graphs were also plotted, and the experimental data of the association phase were fitted by a nonlinear least-squares method to a function of the form of equation 8. When equation 8 is transformed into equation 13:

$$\ln\left(1 - \frac{R(t)}{R_{max}}\right) = -k_{obsd}t \quad (13)$$

plots of $\ln(1-(R(t)/Rmax))$ versus t for the experimentally obtained data yielded straight lines. For the $10^{-6}$ M promazine sensorgram, $R^2=1$ was calculated by Excel's linear regression. All other curves yielded comparable results. From the $R=10^{mV/S}-1$ (y axis) versus t (x-axis) sensorgram plots, dR/dt versus R graphs were derived: see eq 11. Also these curves showed good linearity over the whole range, with $R^2$ values as calculated by Excel exceeding 0.96. Finally, a plot of $k_{on}c_{analyte}+k_{off}$ (slope; see equation 12) versus $c_{analyte}$ yielded a straight line of the form:

slope (min$^{-1}$)=(6.0 10$^6$)$c_{analyte}$+2.19 with $R^2$=0.9997

From this equation, $k_{on}$ and $k_{off}$ can be obtained as $k_{on}$=6.0×10$^6$ min$^{-1}$ M$^{-1}$, $k_{off}$=2.19 min$^{-1}$, calculating
$K_{assoc}$=$k_{on}/k_{off}$=2.74×10$^6$ M$^{-1}$ This corresponds to a ΔG value of interaction of promazine with the sensor surface material of 8.78 kcal mol$^{-1}$.

Figure 3:
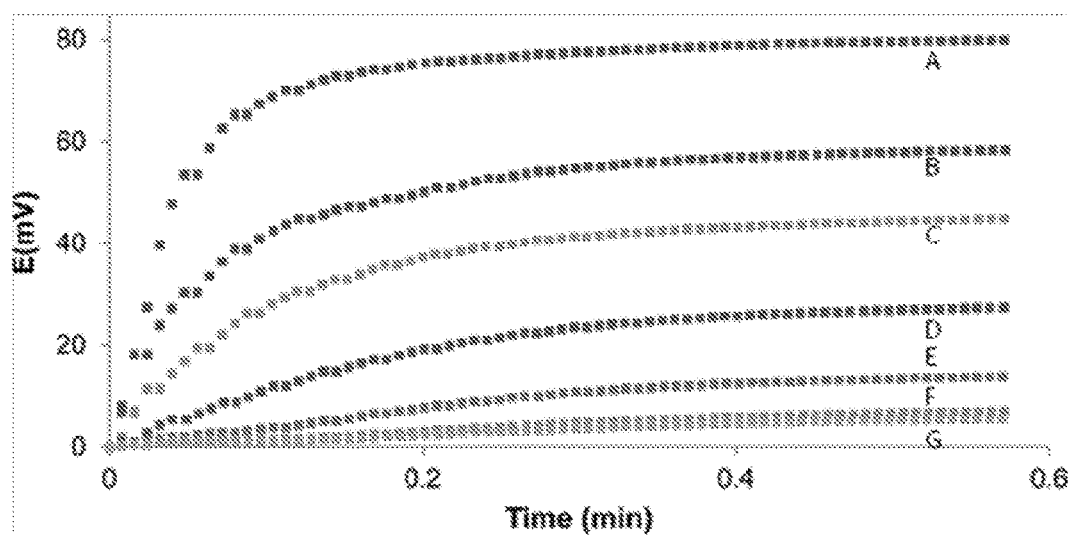
FIG. 3 shows "on" kinetics obtained for tartaric acid on a "gelatin A"-coated sensor for injected concentrations of 1.00, 0.316, 0.100, 0.0316, 0.0100, 0.00316, and 0.00100 mM, as curves A, B, C, D, E, F and G respectively. Only the "on" kinetics part and the plateau values are shown. These graphs were the basis of the linearization method described in the text.

Linearization Method Applied to a Gelatin Coating/Tartaric Acid System:

The same approach was done for tartaric acid, injected on a gelatin A-coated sensor. This gelatin consists of a collagen (proteinaceous) material. The on phases of the sensorgrams are shown in FIG. 3. They are also given with a millivolt y axis to show them in one figure.

After conversion of the y axis from millivolts to $10^{mV/S}-1$, the sensorgrams from FIG. 3 were processed with the linearization method, as described in the previous section. The finally obtained equation of the slope ($k_{on}c_{analyte}+k_{off}$) values versus $c_{analyte}$ was:

slope=4.0×10$^6$$c_{analyte}$+2.83 with $R^2$=0.9995

From the calculated slope and intersection data, we can calculate the kinetic and thermodynamic parameters:

$k_{on}$=4.0×10$^6$ M$^{-1}$ min$^{-1}$, $k_{off}$=2.83 min$^{-1}$, and
$K_{assoc}$=1.42 10$^6$ M$^{-1}$ This corresponds to a ΔG value of interaction of tartaric acid with the sensor surface material of 8.25 kcal mol$^{-1}$.

Comparable data have been obtained under analogous conditions for other anionic (malonic- and maleic acid) organic compounds.

Figure 5:
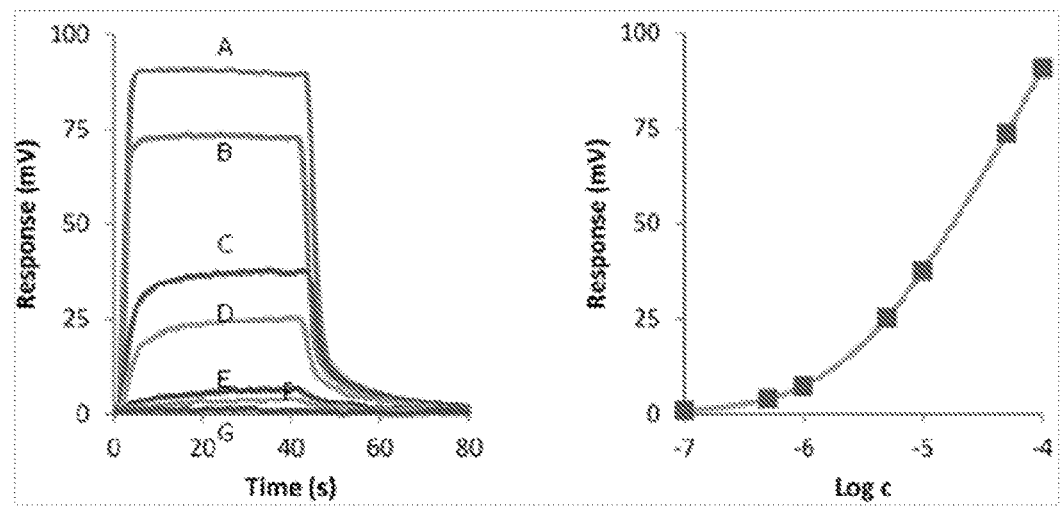
FIG. 5 shows the potentiometric responses (mV) of $10^{-4}$ M (curve A), $3\times10^{-5}$ M (curve B), $10^{-5}$M (curve C), $3\times10^{-6}$ M (curve D), $10^{-6}$ M (curve E), $3\times10^{-7}$ M (curve F) and $10^{-7}$ M (curve G) lidocaine injections in FIA. The responses (in mV) are shown as a function of time (left) and as a function of the logarithm of the concentration (right).

Linearization Method Applied to a Rubber Phase Coating/Lidocaine System:

FIG. 5 shows the sensorgrams observed when different concentrations of lidocaine were injected as a square concentration pulse in a FIA system. The "association", or "on" phase, the plateau region ($R_{max}$), and the "dissociation" or "off" phase are clearly visible in FIG. 5, left graph. If all the $R_{max}$ values (responses measured in the plateau region) are plotted as a function of the logarithm of the concentration, the typical Nicolskii-Eisenmann curve is obtained as shown in FIG. 5, right graph. The curve is the result of a "solver" (Excel) non-linear least squares minimization curve fitting to a Nicolskii-Eisenmann function of the type E=E°+S Log(c+ Cst): see equation 3. From this plot, Solver calculated values of E° of 326 mV, S of 59.1 mV and Cst of 0.0000030.

Figure 6:
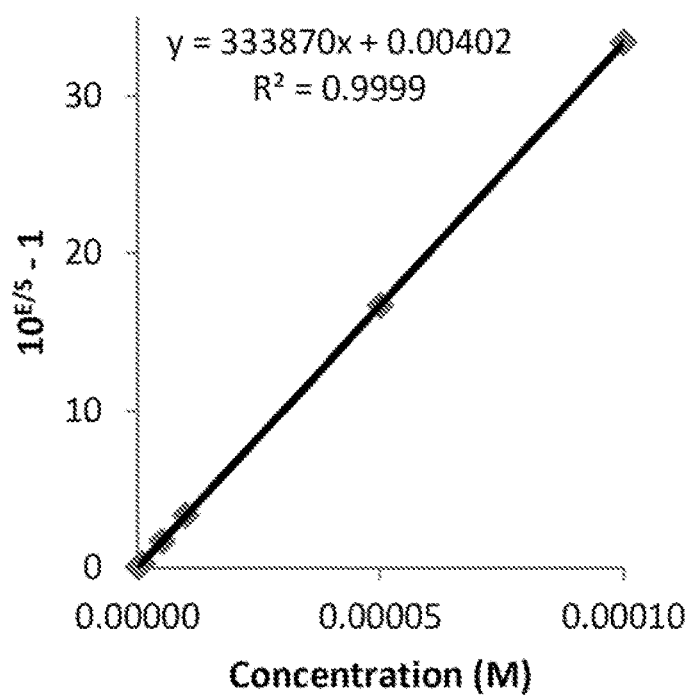
FIG. 6 shows the potentiometric responses of $10^{-4}$ to $10^{-7}$ M lidocaine injections (values measured at the plateau of the sensorgrams) in FIA after transformation to a concentration-related signal, as a function of injected concentration.
Figure 7:
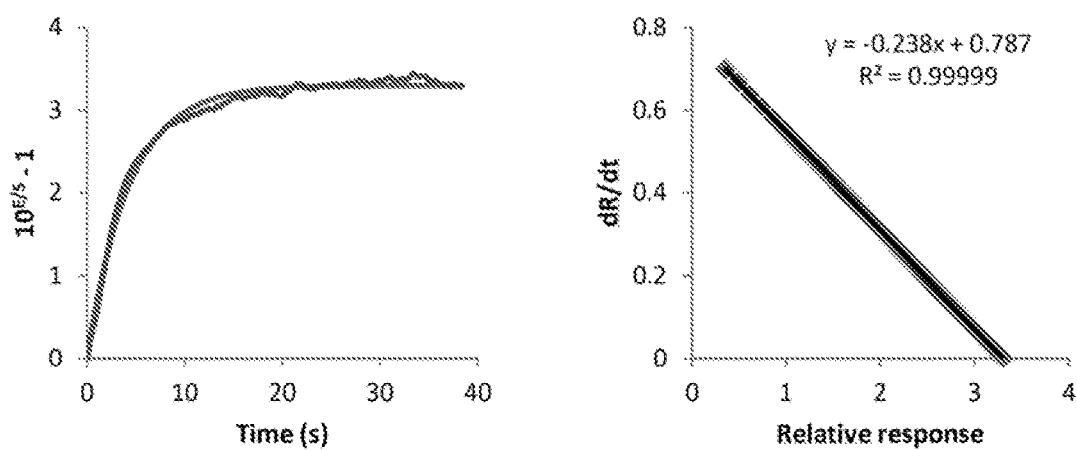
FIG. 7 shows experimental data of the "association" or "on" curve of $10^{-5}$ M lidocaine. The $R(t)=R_{max}(1-e^{-k_{obs}t})$ function was checked with Solver (left graph). R(t) being the response—not as mV, but as $10^{mV/S}-1$, which is analyte concentration related: see text. The right part is a graphical representation of equation 11.

A $R=10^{mV/S}-1$ conversion was then plotted. This is a transpose of the Nicolskii-Eisenmann equation (see equation 4), which is linearly related to the analyte concentration, see FIG. 6. The experimental data of the "association" phase were fit by a non-linear least squares method to a function of the form of $R(t)=R_{max}(1-e^{-k_{obs}t})$ (FIG. 7). When transformed to $$\ln\left(1 - \frac{R(t)}{R_{max}}\right) = -k_{obs} \cdot t,$$

plots of $$\ln\left(1 - \frac{R(t)}{R_{max}}\right)$$

versus t for the experimentally obtained data yielded straight lines. When applied to the "on" phase data of the $10^{-5}$M lidocaine sensorgram (FIG. 7 left), $R^2$=0.999 was calculated by Excel's linear regression. All the other curves at different concentrations yielded comparable results.

Figure 8:
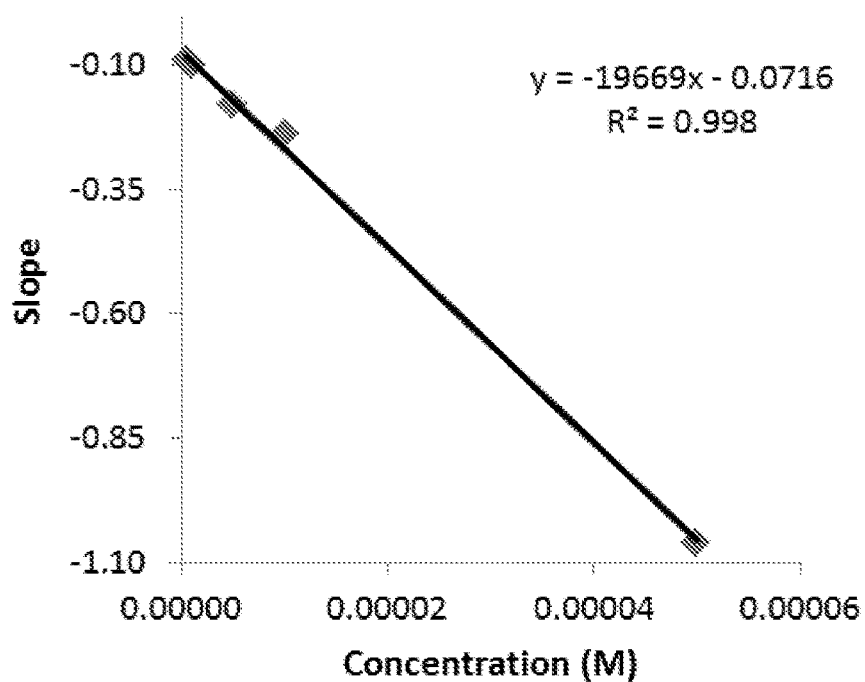
FIG. 8 is a plot of the slope ($=-k_{on}\cdot c_{analyte}+k_{off}$) of the straight line in FIG. 7, right, as a function of the concentration of lidocaine. These slopes were measured at four different lidocaine concentrations.

From the R=$10^{mV/S}$-1 (y axis) versus t (x axis) "on" parts of the sensorgram plots, was derived dR/dt versus R plots. These should yield straight lines as predicted by equation 11. Good linearity was observed over the whole concentration range, with $R^2$ values as calculated by Excel to exceed 0.99. The slope of this line equals $-(k_{on} \cdot c_{analyte}+k_{off})$. Finally, a plot of $-(k_{on} \cdot c_{analyte}+k_{off})$ versus $c_{analyte}$, yielded a straight line of the form: slope (s$^{-1}$)=$-1.97 \times 10^4 \cdot c_{analyte}-0.0716$, with $R^2$=0.998 (FIG. 8) giving $k_{on}$=1.18×10$^6$ min$^{-1}$ M$^{-1}$, $k_{off}$=4.30 min$^{-1}$ and $K_{assoc}$=$k_{on}/k_{off}$=2.75×10$^5$ M$^{-1}$, which corresponds to a $\Delta G$ value for the interaction of lidocaine with the sensor surface material of 7.29 kcal mol$^{-1}$.

Figure 9:
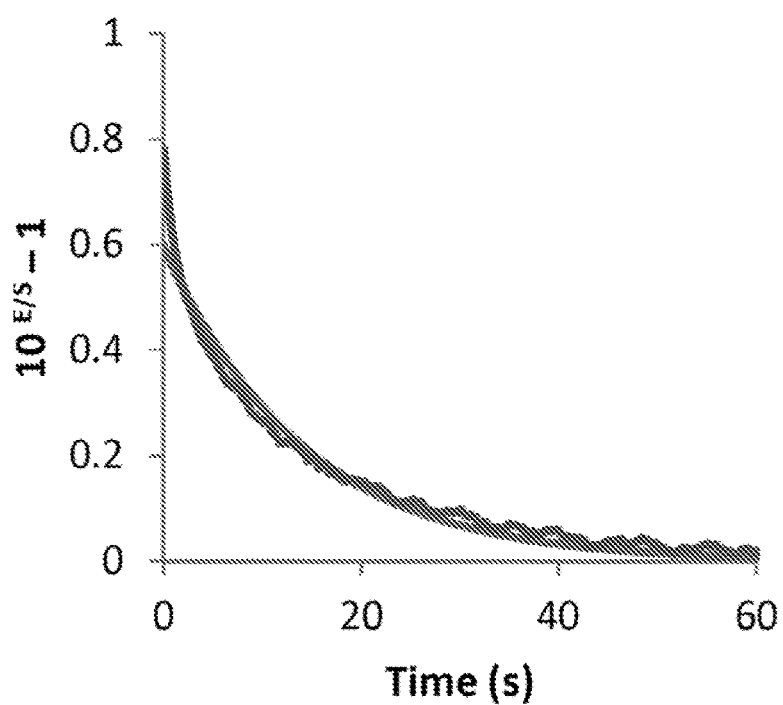
FIG. 9 shows the experimental data of the "off" curve of $10^{-5}$ M lidocaine. The $R(t)=R_{max}(e^{-k_{obs}t})$ function (jagged curve) was fitted by Solver (smooth curve).

The experimental data of the "dissociation" or "off" phase were fit by a non-linear least squares method to a function of the form of R(t)=$R_{max}(e^{-k_{obs}t})$ and fit with Solver (FIG. 9). The $k_{obs}$ value obtained for lidocaine at a 10$^{-5}$M concentration from these data was 0.0721 s$^{-1}$ or 4.33 min$^{-1}$. This perfectly fits the value as calculated above from the "on" phase kinetics (4.30 min$^{-1}$). All other curves at different concentrations yielded comparable results with an average value of $k_{off}$ of 4.49 min$^{-1}$ (St. Dev.: 0.526 min$^{-1}$).

Comparable data have been obtained in analogous conditions for other cationic (Noscapine and Ritodrine) organic compounds.

Linearization Method Applied to a Gelatin Coating Incorporating DA-Aptasensor/Dopamine System:

Morphology:

The covalent binding of the aminated oligonucleotides to the Gelatin B, which contains carboxyl groups, was examined by confocal microscopy. To exclude the background signal, pure Gelatin B and Gelatin B treated with coupling agents (EDC and NHS), were checked as blanks. No signal was observed in the latter cases. This is in contrast with the bright fluorescent signal observed for a hydrogel treated with a fluorescent labeled (Cy3) aminated aptamer. Even after three hours of use in the FIA potentiometric set-up, the intense fluorescence persisted. This experiment confirmed the covalent coupling of the aminated oligonucleotides to the gelatin B.

Figure 10:
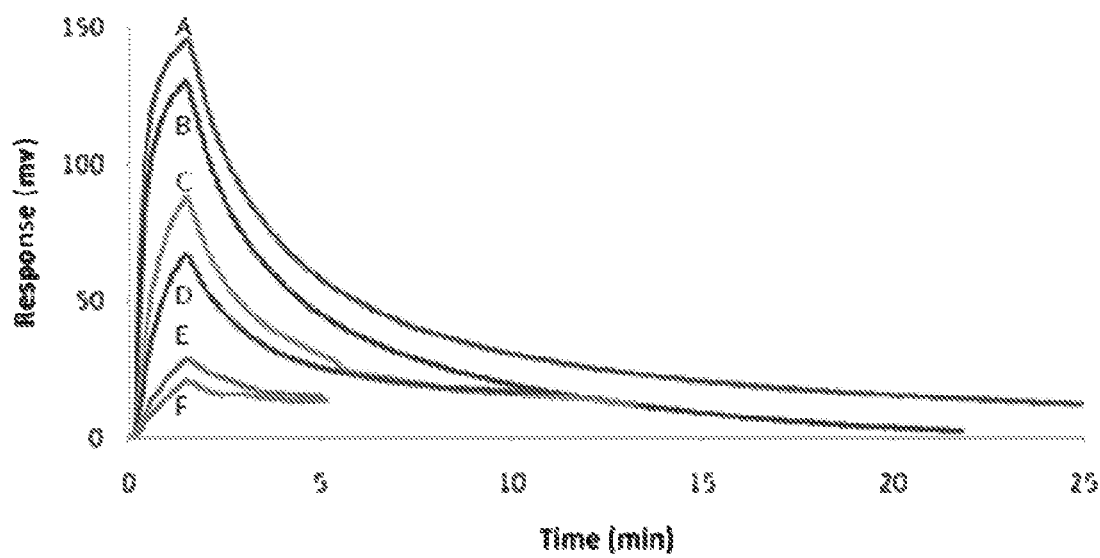
FIG. 10 shows sensorgram recordings for DA on a biosensor with a Gelatin B membrane with covalently linked aptamer. Square concentration pulses were injected for 80 s. The concentration varied from $5\times10^{-7}$ M (curve F) to $10^{-6}$ M (curve E), $5\times10^{-6}$M (curve D), $10^{-5}$M (curve C), $5\times10^{-5}$M (curve B), and $10^{-4}$M (curve A).

Electrochemical Behaviour:

After checking the coupling of the aptamer to the biopolymer as described above, the electrodes were placed in a FIA potentiometric setup. FIG. 10 shows the potentiometric response of DA on the sensor which contains the DA specific aptamer. Higher concentrations of DA show faster "on" kinetics than lower concentrations. This concentration-dependent difference in adsorption kinetics (rising part of the curve) is also typical for SPR experiments. The response heights (mV obtained at the plateau values) are concentration dependent: see FIG. 10.

Figure 11:
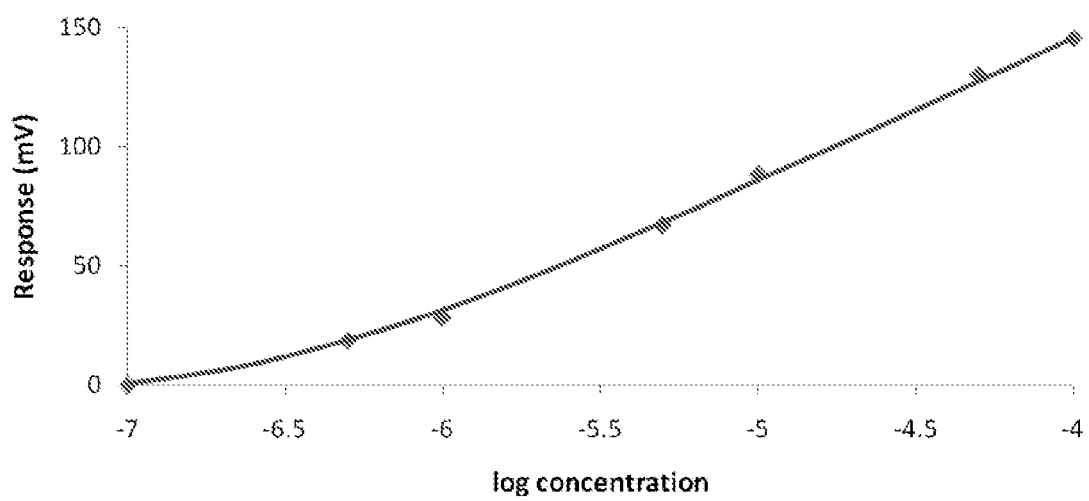
FIG. 11 shows a Nicolskii-Eisenmann-type calibration graph for dopamine on a DA-aptamer doped sensor. It is a plot of the maximum responses (in mV) measured in the sensorgrams (see FIG. 11), versus the concentration. The smooth curve is obtained from a nonlinear least-squares fit to a Nicolskii-Eisenmann function of the type $E=E°+S\cdot\log(c_{DA}+Cst)$. $E°=387.0$ mV, $S=60.39$ mV and $Cst=3\times10^{-7}$ mV.

If the maximum responses (in mV) are plotted against the logarithm of the concentration, the typical Nicolskii-Eisenmann curve is obtained (see FIG. 11). At higher concentration values (results not shown), saturation of the signal (reaching a plateau value) started to occur. This is ascribed to the fact that a relatively low aptamer concentration (10$^{-4}$M) was used to bind to the hydrogel. DA concentrations below 5×10$^{-5}$M were therefore used in these experiments.

Figure 12:
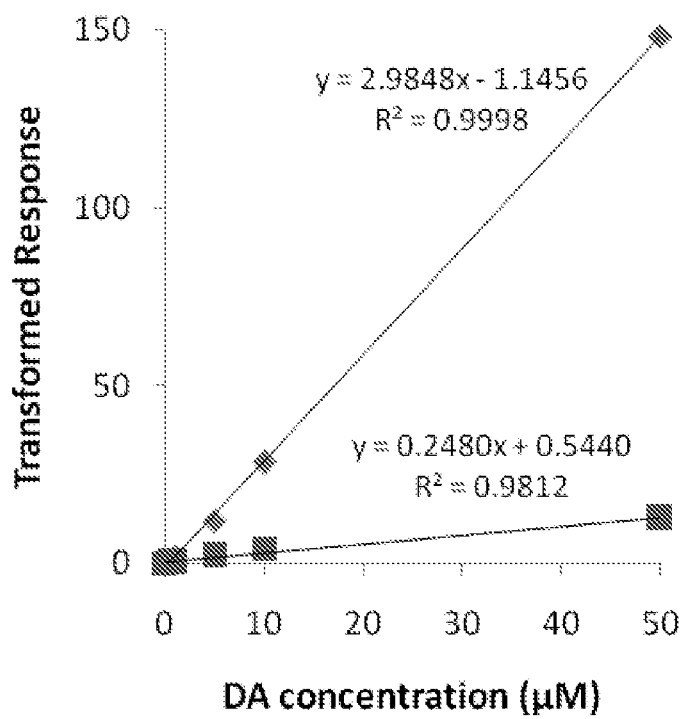
FIG. 12 shows the differences between the aptamer-based potentiometric biosensor (upper curve), and the negative control (lower curve) in respect of the potentiometric responses of $5\times10^{-5}$M to $10^{-7}$ M DA injections in FIA after transformation to a concentration-related signal $10^{mV/S}-1$, see text and equation 4). The upper trendline corresponds to biosensors with aptamer, the lower trendline corresponds to potentiometric sensors which only contain a Gelatin B membrane.
Figure 13:
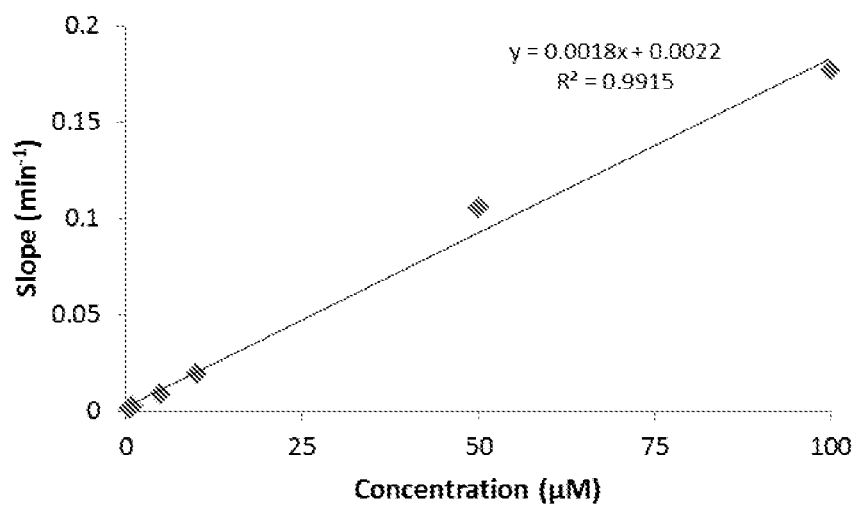
FIG. 13 shows the differences between the aptamer-based potentiometric biosensor (lighter), and the negative control (darker) for injections of DA $10^{-6}$ M on a sensor which contains an aptamer (upper curve: lighter) and on a sensor which does not contain an aptamer (lower curve: darker).

A R=$10^{mV/S}$-1 conversion was then plotted (see equation 4). The $R_{max}$ values (equation 4) of the potentiometric sensors with coupled aptamer were compared with the values obtained with electrodes which did not have an aptamer coupled to the hydrogel: see FIG. 12. Four electrodes were tested, each 3 injections. From five to ten times higher signals were measured with the aptamer-containing electrodes. Not only the height, but also the shape of the sensorgram was different when comparing gelatin B membranes with and without coupled aptamer (see FIG. 13). The gelatin B electrodes containing aptamer always yielded slowly falling curves. This is additional evidence for the recognition of the target molecule by the aptamer. Slowly falling curves mean slow desorption kinetics. This yields small $k_{off}$ values, resulting in high $K_{association}$ values, since $K_{assoc}$=$k_{on}/k_{off}$.

FIGS. 10, 11, 12 and 13 clearly show that the aptamer-based sensors are very sensitive, the responses being at least a factor of 15 higher (on a mV basis) than those of the classical PVC-based electrodes reported in B. Vissers et al., Electrochimica Acta 51(24) (2006) 5062-5069.

Figure 14:
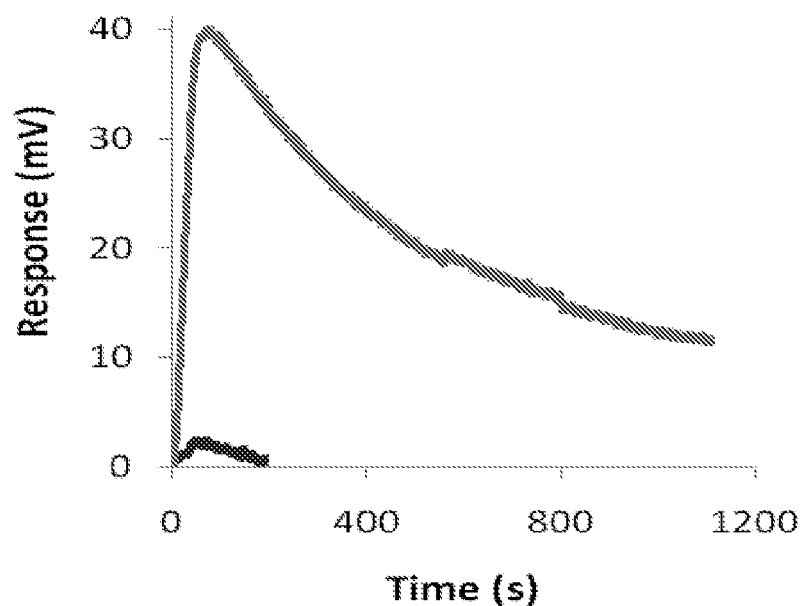
FIG. 14 shows the "Slope" of dR/dt versus R curves (see equation 11) which is plotted against the DA concentrations which were used to record the sensorgrams. The y-axis of the figure shows the slope ($k_{on}\cdot c_{analyte}+k_{off}$).

Determination of the Association Constant $K_{ass}$, Between DA-Specific Aptamer and DA:

Sensorgrams were recorded at different analyte concentrations, see FIG. 10. It is clear from FIGS. 10, 11, 12 and 13 that the above-described model is also applicable to the aptamer-based sensor. FIG. 14 confirms the strong response of the aptamer-based sensor (upper, lighter curve) versus the response of a sensor without aptamer (lower, darker curve). Calculated values of $k_{on}$ (1.27×10$^6$ L.mol$^{-1}$. min$^{-1}$), $k_{off}$ (0.042 min$^{-1}$), $K_{ass}$ (3.04×10$^7$ M$^{-1}$), $K_{diss}$ (3.30×10$^{-7}$ M) and $\Delta G$ (8.69 kcal mol$^{-1}$) were determined. This $K_{diss}$ value was comparable when four different electrodes were tested, namely $K_{diss}$ values of 3.30×10$^{-7}$M, 1.37×10$^{-6}$M, 1.99× 10$^{-6}$ M and 1.58×10$^{-6}$M with a mean value of $K_{diss}$=1.31× 10$^{-6}$ M (standard deviation=4.93×10$^{-7}$M). The obtained $K_{diss}$ is similar to the value (7×10$^{-7}$M) determined colorimetrically by Zheng (2011). This, to our knowledge, is the first time that molecular interaction data were obtained for the interaction of a biomolecule (the aptamer) with its target molecule, via a potentiometric sensor principle.

Specific Detection with DA-Specific Aptamer:

To check the specificity of the DA-specific aptamer, dopamine and three other basic drugs (ritodrine, lidocaine and promazine) were tested on the gelatin B-coated electrodes with and without the aptamer. These lipophilic cationic drugs have much better responses on PVC-based potentiometric sensors (Vissers et al.) than DA. Sensors based on gelatin B were quite insensitive towards these drugs, there being no improvement in sensitivity for these compounds when the aptamer bio-recognition element was coupled to the gelatin B, whereas DA showed a very clear increase in $R_{max}$, as disclosed above. Table 1 gives the $R_{max}$ values (in mV) of 10$^{-5}$M injections of different analyte molecules for different potentiometric electrodes.

TABLE 1

| Coating | Dopamine: response in mV | Ritodrine: response in mV | Lidocaine: response in mV | Promazine: response in mV |
| --- | --- | --- | --- | --- |
| Gelatin B | 9.46 | 1.83 | 2.88 | 3.66 |
| Gelatin B + DA-specific aptamer | 92.86 | 1.57 | 1.57 | 2.44 |

Discussion:

The sensors were continuously regenerated as the eluent was running at a 1 mL min$^{-1}$ flow-rate. It was not necessary to use a regeneration buffer to have the baseline return to its original position. Occasionally, slight irreversible phenomena occurred as indicated by an increased baseline after the desorption step. This occasional phenomenon may be due to a badly prepared coating. The phenomenon was observed more frequently with the gelatin-type coatings than with the rubber-type coatings. The rubber-type coatings are very robust with lifetimes exceeding several months. The gelatin-type coatings could only be used for about one week.

All systems studied yielded comparable Gibbs free energies of interaction, which are in the expected range for secondary interactions. This does not mean that all sensors respond with equal sensitivity: see FIGS. 4, 5 and 11. From FIG. 4, the following data is adduced by fitting the measured values to equation 3: promazine, $E^0$=443 mV, S=65.7 mV, Cst=1.79×10$^{-7}$; tartaric acid, $E^0$=186 mV, S=35.9 mV, Cst=8.40×10$^{-6}$.

Potentials occurring at the solution-sensor interface are not only determined by the strength of interaction between the analyte molecule and the molecules in the sensor surface, but also by the charge density σ which can be obtained on the sensor's surface. The relation between charge surface density σ and surface potential $\psi_0$ can be expressed by a simplified form of the Grahame equation (see Butt, H. J., Graf, K., Kappl, M., Physics and Chemistry of Interfaces; Wiley-VCH Verlag GmbH: Weinheim, Germany, 2006; Israelachvili, J. N., Intermolecular and Surface Forces; Academic Press, Elsevier: London, 2011; and Fritz, J.; Cooper, E. B.; Gaudet, S.; Sorger, P. K.; Manalis, S. R., Proc. Natl. Acad. Sci. U.S.A. 99 (2002) 14142-14146.

$$\sigma = \frac{\varepsilon\varepsilon_0\psi_0}{\lambda_D} \qquad (14)$$

$\lambda_D$ is the Debye distance. The exact interplay between charge surface density (equation 14) and Gibbs free energies of interaction and their combined effect on potential formation (equation 3) needs further theoretical and experimental investigation.

Figure 15:
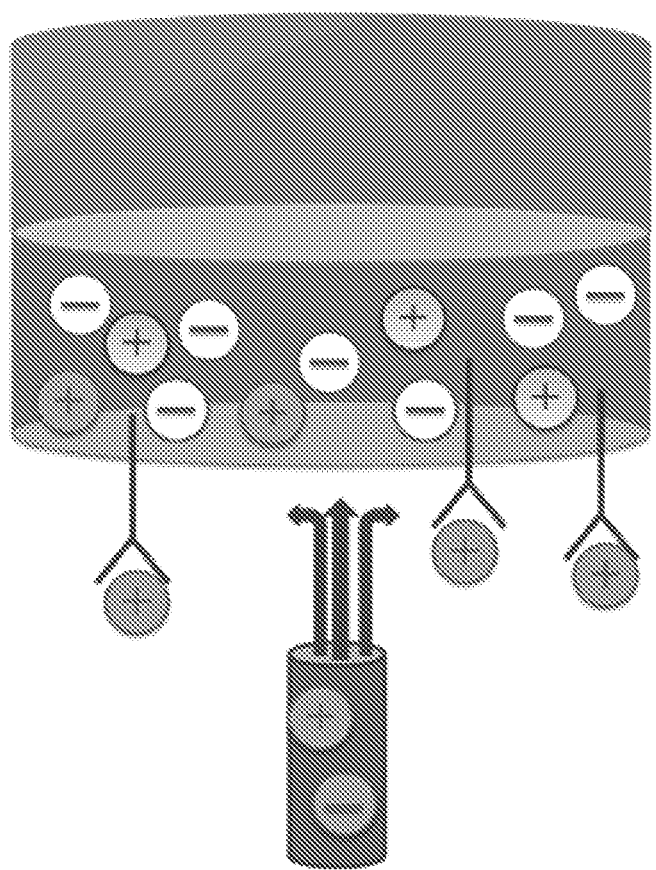
FIG. 15 shows the possible fate of an analyte cation contacting a cation exchange-type sensor coating. When the ionically conducting layer receives a pulse of analyte ions, these ions can adsorb to receptor sites or to polymer materials or they can form ion-ion interactions (rapid processes). They can also perform ion exchange with countercations in the ionically conducting layer (slow process). Possible binding (adsorption) sites are indicated by a reversed "Y".

At equal surface charge densities σ and permittivities, one expects ΔG to be the determining factor, as chemical interaction energy is converted into nonfaradic electrical energy by the well-known equation ΔG=−nFE, giving rise to a potential E. ΔG is the difference in Gibbs free energy of the analyte ion between the running buffer phase and the membrane sensor phase (indexed $\Delta G_{tr}$, for "transfer"): see FIG. 15 and equation 15.

$$\Delta G_{tr} = \Delta G_{hydr} - (\Delta G_{solv} + \Delta G_{ion} + \Delta G_{complex}) = -nFE \qquad (15)$$

The analyte ion's Gibbs free energy in the running buffer is determined mainly by hydration ($\Delta G_{hydr}$). In the ion exchange material, solvatation ($\Delta G_{solv}$, van der Waals binding to polymer or plasticizer materials), ion pair formation ($\Delta G_{ion}$, ion-ion interaction with the lipophilic anion in the membrane), and receptor binding ($\Delta G_{complex}$) could be the potential-determining factors.

What is measured is a mix of all these factors. If only complex formation with a receptor (bait) molecule is of interest, just as in SPR methods, coating materials have to be chosen which have small interactions with the analyte (prey) molecule (second molecular species).

In the small time period (40 s) of contact between the analyte (second molecular species) and the sensor coating (comprising the first molecular species), adsorption phenomena can be predominant over other phenomena such as diffusion into the sensing layer and ion exchange. This is a preferred situation (also in SPR), yielding on/off kinetics of the studied systems responding to simple exponential functions (equations 8 and 10). Diffusion from the analyte solution to the sensor coating surface is a faster process than the adsorption processes studied here (see Lovich, M. A.; Edelman, E. R. Biophys. J., 70 (1996) 1553-1559) and can be kept to a minimum by choosing the appropriate hydrodynamic conditions. Some analyte compounds (second molecular species) other than those studied here can behave in a more complex manner, pointing to diffusion into the sensor coating. This manifests itself by more complex on and off kinetics, which is described by changing t in equations 8 and 10 by √t (typical for diffusion-controlled systems).

Coating materials such as gelatin are easily doped by proteins [see De Wael, K.; De Belder, S.; Van Vlierberghe, S.; Van Steenberge, G.; Dubruel, P. Talanta 82 (2010) 1980-1985] antibodies, bioparticles (viruses, bacteria, . . . ), DNA, and aptamers. Large biomolecules can be used as analyte (prey ligand) (second molecular species). From experience with oligonucleotides [Nagels, L. J.; Everaert, J.; Bohets, H.; Del Favero, J.; Goossens, D.; Robbens, J.; Pietraszkiewicz, M.; Pietraszkiewicz, O., Comb. Chem. High Throughput Screening 10 (2007) 555-559] it is known that these multiply charged molecules give very good potentiometric responses. For example, the 22-mer 5'-AAAATAT-CATCTTTGGTGTTTC-3' yields a slope (S, equations 2 and 3) value of 38 mV per decade, which is much higher than that calculated by the Nernst equation (equation 2). This is due to the fact that equation 2 was derived for point charges, while an oligonucleotide is a multiply charged rodlike molecule. It is detected three times more sensitively (on a molar basis) than a small, well-responding anionic molecule such as maleic acid. The sensorgram shape of the above-mentioned oligonucleotide is comparable to those described here for smaller molecules (for a 10$^{-5}$ M injection, exponential behavior was observed in the "on" as well as in the "off" phase, with $k_{obsd}$ being 0.055 s$^{-1}$ and $k_{off}$ being 0.032 s$^{-1}$). This means that the described method can also be used to measure DNA/DNA interactions. Potentiometry also allows working with miniaturized electrode arrays (eventually with ion-sensitive field-effect transistor (ISFET) readout), which means that high-throughput measurements can be considered.

It is to be understood that although preferred embodiments, specific constructions and configurations, as well as materials, have been discussed herein for devices according to the present invention, various changes or modifications in form and detail may be made without departing from the scope and spirit of this invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A coated-wire potentiometric sensor comprising an electronically conducting substrate electrode coated with an ionically conductive sensing layer and an outermost surface consisting of or comprising in and/or on a first molecular species which is capable of reversibly adsorbing a second molecular species.

2. The potentiometric sensor according to claim 1, wherein said outermost surface is adapted with a coating immobilising said first molecular species.

3. The potentiometric sensor according to claim 2, wherein said coating is a hydrogel coating.

4. The potentiometric sensor according to claim 3, wherein said hydrogel coating is a collagen-based hydrogel.

5. The potentiometric sensor according to claim 1, wherein at least one of said first and second molecular species is selected from the group consisting of proteins, antibodies, bioparticles, DNA, and aptamers.

6. The potentiometric sensor according to claim 1, wherein said outermost surface is adapted with a coating on which said first molecular species is adsorbed.

7. The potentiometric sensor according to claim 6, wherein said coating is a hydrogel coating.

8. The potentiometric sensor according to claim 7, wherein said hydrogel coating is a collagen-based hydrogel.

9. The potentiometric sensor according to claim 1, wherein said outermost surface is adapted with a lipophilic rubber-based coating.

10. The potentiometric sensor according to claim 1, wherein said outermost surface is adapted with a collagen-based hydrogel coating.

11. A method for measuring the affinity between a first molecular species and a second molecular species comprising the steps of:
providing a potentiometric sensor of the coated-wire type as set forth in claim 1;
placing said sensor in a system for the recording of sensorgrams;
recording a sensorgram of the adsorption of a second molecular species on said first molecular species of or comprised in and/or on said outermost surface.

12. The method according to claim 11, wherein said outermost surface is provided with a coating immobilising said first molecular species.

13. The method according to claim 12, wherein said coating immobilising said first molecular species is a lipophilic rubber-based coating.

14. The method according to claim 12, wherein said coating immobilising said first molecular species is a hydrogel coating.

15. The method according to claim 11, wherein said outermost surface is adapted with a coating on which said first molecular species are adsorbed.

16. The method according to claim 11, wherein said outermost surface is adapted with a lipophilic rubber-based coating.

17. The method according to claim 11, wherein said outermost surface is adapted with a collagen-based hydrogel coating.

18. The method according to claim 11, wherein said system is a hydrodynamic wall-jet system.

19. The method according to claim 11, wherein at least one of said first and second molecular species is selected from the group consisting of target molecules for biorecognition elements, macrocycles, ionophores, proteins, antibodies, bioparticles, DNA, and aptamers.

20. The method according to claim 11, wherein at least one of said first and second molecular species is a bio-active molecule.

21. The method according to claim 20, wherein said bio-active molecule is a physiologically active compound or a nutritionally active compound.

22. The method of claim 20, wherein said bio-active molecule is a pharmacologically active agent.

23. A process using a coated-wire potentiometric sensor as set forth in claim 1 comprising measuring the surface concentration of a second molecular species on the outermost surface of the potentiometric sensor by converting the millivolt sensor responses to the concentration of said adsorbed second molecular species.

24. The process according to claim 23, wherein said potentiometric sensor is used to measure the adsorption of said second molecular species on said adapted outermost surface as a function of time.

25. The process according to claim 23, wherein said concentration of said second molecular species as a function of time is linearized and analysed on the basis of a pseudo-first order-kinetic model of adsorption to provide the $k_{on}$, the rate of association of said second molecular species to said first molecular species, $k_{off}$, the rate of dissociation of said second molecular species from said first molecular species, and $K_{assoc}$, the equilibrium coefficient of association of said second molecular species to said first molecular species.

* * * * *